United States Patent
Luo et al.

(10) Patent No.: US 8,288,306 B2
(45) Date of Patent: Oct. 16, 2012

(54) PREPARATION PROCESS OF A CATALYST USED FOR GAS PHASE OXIDATION OF LIGHT ALKENES TO UNSATURATED ALDEHYDES

(75) Inventors: Ge Luo, Shanghai (CN); Xin Wen, Shanghai (CN); Xiaoqi Zhao, Shanghai (CN); Xuemei Li, Shanghai (CN); Yan Zhuang, Shanghai (CN); Jianxue Ma, Shanghai (CN); Jingming Shao, Shanghai (CN)

(73) Assignee: Shanghai Huayi Acrylic Acid Co., Ltd., Pudong District, Shanghai (CN)

( * ) Notice: Subject to any disclaimer, the term of this patent is extended or adjusted under 35 U.S.C. 154(b) by 4 days.

(21) Appl. No.: 12/690,764

(22) Filed: Jan. 20, 2010

(65) Prior Publication Data

US 2010/0323881 A1    Dec. 23, 2010

(30) Foreign Application Priority Data

Jun. 22, 2009    (CN) .......................... 2009 1 0053548

(51) Int. Cl.
| | |
|---|---|
| *B01J 27/228* | (2006.01) |
| *B01J 21/02* | (2006.01) |
| *B01J 21/00* | (2006.01) |
| *B01J 23/00* | (2006.01) |
| *B01J 23/02* | (2006.01) |
| *B01J 23/06* | (2006.01) |

(52) U.S. Cl. ........ 502/179; 502/202; 502/204; 502/205; 502/206; 502/207; 502/232; 502/240; 502/246; 502/247; 502/248; 502/249; 502/250; 502/251; 502/254; 502/255; 502/256; 502/305; 502/306; 502/311; 502/312; 502/340; 502/353

(58) Field of Classification Search ........... 502/305–355
See application file for complete search history.

(56) References Cited

U.S. PATENT DOCUMENTS

| | | | | |
|---|---|---|---|---|
| 3,936,505 | A * | 2/1976 | Oda et al. ...................... | 502/215 |
| 3,951,861 | A * | 4/1976 | Shiraishi et al. .............. | 502/178 |
| 4,217,309 | A * | 8/1980 | Umemura et al. ............ | 568/477 |
| 4,537,874 | A * | 8/1985 | Sato et al. ..................... | 502/311 |
| 5,132,269 | A * | 7/1992 | Sasaki et al. .................. | 502/205 |
| 6,080,893 | A * | 6/2000 | Hecquet et al. ............... | 568/479 |
| 6,383,973 | B1 * | 5/2002 | Kimura et al. ................ | 502/300 |
| 7,473,666 | B2 * | 1/2009 | Yanagi et al. ................. | 502/243 |
| 7,494,952 | B2 * | 2/2009 | Kauffman et al. ............ | 502/305 |
| 7,732,367 | B2 * | 6/2010 | Stevenson et al. ............ | 502/208 |

* cited by examiner

*Primary Examiner* — Patricia L Hailey

(57) ABSTRACT

The present invention provides a preparation process of complex oxides catalyst containing Mo, Bi, Fe and Co, which comprising steps as following: dissolving precursor compounds of the components for catalyst and complexing agent in water to obtain a solution, and then drying, molding and calcining the solution to obtain catalyst. The catalyst is used for gas phase oxidation of light alkenes to unsaturated aldehydes. The catalyst has high activity, selectivity and stability. The reaction condition is mild. The preparation process of the catalyst is easy to operate and can be used for mass production.

20 Claims, No Drawings

PREPARATION PROCESS OF A CATALYST USED FOR GAS PHASE OXIDATION OF LIGHT ALKENES TO UNSATURATED ALDEHYDES

BACKGROUND OF THE PRESENT INVENTION

1. Field of Invention

The present invention relates to a preparation process of a complex oxide catalyst and the application thereof for gas phase oxidation of light alkenes to unsaturated aldehydes.

2. Description of Related Arts

Acrylic acid and methacrylic acid are two kinds of important organic chemical product, which are currently prepared via two oxidation reactions of corresponding alkenes. For example, firstly the propylene is selectively oxidized to acrolein, and subsequently oxidized to acrylic acid; isobutene or tert-butyl alcohol is selectively oxidized to methacrolein, and subsequently oxidized to methacrylic acid. Whatever producing acrylic acid or methacrylic acid, the development of high performance catalyst for the first step, that is, alkenes oxidation to corresponding unsaturated aldehydes, is one of the core techniques of the whole process.

Till now, the reported catalysts used for selective oxidation of light alkenes to unsaturated aldehydes usually are complex oxide catalysts adopting Mo, Bi, Fe and Co as main active components. A few trace elements are added to the components as promoters to further improve the activity and selectivity of the catalyst. Therefore, the components of the catalyst are very complex, and may be up to 10 types. The complexity of the components provokes a series of problems. The most prominent problem is that the precursor salts of the elements contained in the catalyst have remarkable difference on solubility in water, which will result in uneven distribution of the catalyst components and affect the performance of the catalyst directly, such as activity, selectivity and life span of the catalyst.

Nowadays, the complex oxide catalysts used for selective oxidation of light alkenes to unsaturated aldehydes are often prepared via coprecipitation method, which needs dissolving precursor salts of the catalyst in water. Some compounds of elements, such as Co and Fe, have high solubility, so as to be easily dissolved; some have low solubility, such as the compounds of tungsten, stibium and niobium mentioned in the U.S. Pat. Nos. 5,208,371, 4,816,603 and CN1131059A. In order to dissolve theses compounds of low solubility, huge amount of water has to be used. However, a huge amount of heat has to be needed to dry the solution or slurry containing the compound in the subsequence process, which causes a lot of waste. Besides, for some compounds that can be easily hydrolyzed, such as compounds of Bi, a huge amount of water is unfavorable. In order to solve this problem, the patent JP57-12827 adds some acids, such as $HNO_3$, HCl and so on, during the process of catalyst preparation to make the pH value thereof lower than 7, so that the precursor salts of the catalyst can be dissolved evenly. The U.S. Pat. No. 4,224,193 further lower the pH value of the system to a range of 1 to 5. However, these methods are very complex to operate in industry, the excess acids can corrode the reaction device, and a huge amount of toxic gas $NO_x$ is produced during the drying and calcining process of the catalyst preparation. The patent EP0420048 strictly controls the amount of $HNO_3$ added, that is to say greatly reduce the amount of $HNO_3$ that is being used, but this problem still has not been solved.

In order to avoid uneven distribution of the catalyst components due to different solubility of the precursor of the catalyst, U.S. Pat. Nos. 5,138,100, 5,583,086 and CN1486787 change the preparation method of the catalyst by dividing the components into two groups according to the different solubility, separately dissolving the two groups of compounds and mixing the two solutions together. This method can improve the performance of the catalyst, but still can cause the uneven of the catalyst components during the mixing process. Moreover, the preparation process becomes more complex, and is not easy to operate in industry.

Therefore, the above-mentioned patents did not solve the uneven problem of the catalyst component due to the different solubility of the precursor salts.

Furthermore, during the first oxidation reaction of alkene to acrylic acid or methacrylic acid, the conversion and selectivity will greatly affect the whole preparation process. Especially in the process of isobutene to methacrylic acid, the unreacted isobutene in the first oxidation reaction will poison the catalyst of the second oxidation reaction of methacrolein to methacrylic acid. Therefore, in order to retain a long and stable operation, the reaction of propylene to acrolein and isobutene or tert-butyl alcohol to methacrolein must use highly active catalyst or run under high temperature, which will lower the selectivity to the unsaturated aldehydes and reduce the life span of the catalyst. The U.S. Pat. Nos. 4,217,309, 4,250,339, 4,258,217 and 4,267,385 cannot obtain high selectivity to methacrolein under the high conversion of isobutene. Therefore, how to operate the reaction under a milder temperature and retain the high activity, selectivity and stability of catalyst is urgent to be solved.

In order to solve the above-mentioned two problems, one is the uneven catalyst components caused by different solubility of the precursor catalyst which worsen the performance of the catalyst, and the other one is the high conversion, selectivity and stability of the catalyst cannot be obtained simultaneously, the present invention provides a new preparation process of this type of catalyst. A catalyst of high activity and selectivity can be obtained by adding a complexing agent during the dissolving process of the precursor salts, so that the oxidation reaction can be done under a milder condition, the life span of the catalyst is prolonged, and the preparation process is easy to operate so as to be suitable to mass production.

SUMMARY OF THE PRESENT INVENTION

An object of the present invention is to provide a preparation process of a catalyst used for selective oxidation of light alkenes to unsaturated aldehydes. The precursor compounds for preparing catalyst are mixed evenly due to the presence of the complexing agent, and then are dried, molded and calcined. The catalyst used for selective oxidation of light alkenes to unsaturated aldehydes prepared by this method has high activity, selectivity and stability. The preparation process is easy and suitable for mass production.

Accordingly, in order to accomplish the above object, the present invention provides a preparation process of a complex oxide catalyst containing Mo, Bi, Fe and Co. The catalyst with a general formula $x(Mo_{12}Bi_aFe_bCo_cA_dD_eO_f)/yZ$ is used for selective oxidation of light alkenes to unsaturated aldehydes, wherein $Mo_{12}Bi_aFe_bCo_cA_dD_eO_f$ is the active component of the catalyst; Mo, Bi, Fe, Co and O represent molybdenum, bismuth, iron, cobalt and oxygen respectively; A represents at least one selected from a group consisting of Ni, W, V, Zn, Cr, Mn, Sn, Pb, P, B, Te, Ce, La, Nb and Re; D represents at least one selected from a group consisting of K, Rb, Cs, Sr, Mg and Ba; Z is a heat conduction agent of the catalyst, which is added during the molding process of the catalyst preparation; Z is selected from the group consisting of silicon powder, SiC, graphite, carbon fiber, and a mixture thereof; a~e represent the atomic ratio of the corresponding elements respectively, a=0.05~8, b=0.05~10, c=0.5~15, d=0.01~5, e=0.01~3; f is the number of oxygen atoms which satisfies the atomic valences of the other elements; x and y represent the amount of the catalyst active components and the heat conduction agent Z, respectively, y/(x+y)=0~70% (weight).

The preparation process of catalyst comprises steps of:

(a) obtaining a mixed solution by dissolving precursor compounds and complexing agent, and stirring the mixed solution at a temperature of from 40 to 90° C. for 0.5 to 7 hours to obtain a slurry;

(b) drying the slurry obtained in step (a) at a temperature of from 80 to 180° C. for 2 to 12 hours to obtain a dry pulp;

(c) mixing the dry pulp and heat conduction agent and molding the mixture to granules;

(d) calcining the granules at a temperature of from 480 to 550° C. for 2 to 7 hours to obtain the catalyst.

Step (a) can be embodied as step (a'), step (a") or step (a''') illustrated as follows.

Step (a') comprises steps of (a1') dissolving a precursor compound of component Mo and complexing agent in water to obtain solution A';

(a2') dissolving a precursor compound of component Fe, Co, Bi, A and B in water to obtain solution B'; and (a3') mixing solution A' and solution B', and stirring the mixed solution at a temperature of from 40 to 90° C. for 0.5 to 7 hours to obtain a slurry.

Step (a") comprises steps of (a1") dissolving a precursor compound of component Mo in water to obtain solution A";

(a2") dissolving a precursor compound of component Fe, Co, Bi, A, B and complexing agent in water to obtain solution B"; and (a3") mixing solution A" and solution B", and stirring the mixed solution at a temperature of from 40 to 90° C. for 0.5 to 7 hours to obtain a slurry.

Step (a''') comprises steps of (a1''') dissolving a precursor compound of component Mo in water to obtain solution A''';

(a2''') dissolving a precursor compounds of component Fe, Co, Bi, A and B in water to obtain solution B'''; and (a3''') mixing solution A''' and solution B''', adding complexing agent to the mixed solution, and stirring the mixed solution with the complexing agent at a temperature of from 40 to 90° C. for 0.5 to 7 hours to obtain a slurry.

The complexing agent is at least one selected from a group consisting of citric acid, oxalic acid, tartaric acid, lactic acid, ethylenediamine tetraacetic acid, iminodiacetic acid and ethylene glycol diethyl ether diamine tetraacetic acid. The molar ratio of the complexing agent and metal ions of the catalyst is 0.5:1 to 3:1.

Dry the slurry at a temperature of from 70 to 200° C. for 1 to 48 hours to obtain a dry pulp. Preferably, dry the slurry at a temperature of from 80 to 180° C. for 2 to 12 hours to obtain a dry pulp. Then mix the dry pulp and heat conduction agent and mold the mixture to granules. The heat conduction agent is selected from a group consisting of SiC, silicon powder, graphite carbon fiber, and a mixture thereof. The mold of the granules can be accomplished by various ways, such as tableting, extruding, coating and granulating. The shape of the granule can be sphere, hollow column, solid column, trefoil, tetrafoil and gear.

Calcine the molded granule in molecular oxygen-containing gas or molecular oxygen-containing diluted gas at a temperature of from 300 to 600° C. for 1 to 10 hours to obtain catalyst. Preferably, Calcine the molded granule at a temperature of from 480 to 550° C. for 2 to 7 hours. The molecular oxygen comes from pure oxygen, rich oxygen or air, and the diluted gas is one or more selected from a group consisting of $N_2$, $H_2O$, He and Ar. The volume space velocity of gas relative to the catalyst is from 50 to 1500 $h^{-1}$.

The catalyst prepared by the above-mentioned process is used for gas phase oxidation of light alkenes to unsaturated aldehydes, such as the selective oxidation of propylene to acrolein and selective oxidation of isobutene or tert-butyl alcohol to methacrolein. When the catalyst is used for selective oxidation of isobutene or tert-butyl alcohol to methacrolein, the selective oxidation process comprises steps of: preheating mixed gas of isobutene (or tert-butyl alcohol), air or oxygen-containing diluted gas, and steam; subsequently, pumping the preheated gas into a fixed-bed tube reactor to enable the selective oxidation. The reaction temperature is in the range of 300 to 500° C., and the reaction pressure is 0.1 to 0.5 MPa. The space velocity of the raw gas is 1000 to 5000 $h^{-1}$. The molar concentration of isobutene or tert-butyl alcohol is 1 to 20%. The molar ratio of steam to isobutene or tert-butyl alcohol is 1 to 15.

When the catalyst is used for selective oxidation of propylene to acrolein, the selective oxidation process comprises steps of: preheating mixed gas of propylene, air or molecular oxygen-containing diluted gas, and steam; subsequently, pumping the preheated gas into a fixed-bed tube reactor to enable the selective oxidation. The reaction temperature is in the range of 280 to 380° C., and the reaction pressure is 0.1 to 0.5 MPa. The space velocity of the raw gas is 800 to 5000 $h^{-1}$. The molar ratio of $O_2$ to propylene is 1 to 10, and the molar ratio of steam to propylene is 1 to 15.

The calculation formula for conversion of light alkenes and selectivity to unsaturated aldehydes during the reaction is illustrated as follows.

Conversion of light alkenes=mole number of consumed light alkenes/mole number of fed light alkenes*100%

Selectivity to unsaturated aldehydes=mole number of produced unsaturated aldehydes/mole number of consumed light alkenes*100%

DETAILED DESCRIPTION OF THE PREFERRED EMBODIMENT

The present invention is further illustrated through the following embodiments, without limiting the scope of the claims.

EXAMPLE 1-5

Dissolve 1000 g ammonium heptamolybdate in 2 liter distilled water to obtain solution A; Dissolve 297.6 g bismuth nitrate pentahydrate, 192.6 g ferric nitrate ninehydrate, 755.5 g cobalt nitrate hexahydrate, 27.5 g nickel nitrate hexahydrate, 9.5 g potassium nitrate, and 5.5 g cesium nitrate in 1.5 liter distilled water to obtain solution B. Add solution A into solution B and add complexing agent into the mixture of solution A and solution B, and keep stirring at 60° C. for 5 hours to obtain a slurry. Then transfer the slurry into an oven of 100° C. for 18 hours to obtain a dry pulp. Mix 70 g dry pulp and 30 g SiC powder mechanically, and mold the mixture into hollow column shape granules with 5 mm outer diameter, 2 mm inner diameter and 5 mm length. Calcine the granules in air to obtain a catalyst of $70(Mo_{12}Bi_{1.3}Fe_1Co_{5.5}Ni_{0.2}K_{0.2}Cs_{0.06})/30SiC$.

The complexing agent, the dose thereof, and the calcining conditions of example 1-5 are shown in Table 1.

TABLE 1 dose of the complexing agent and calcining conditions of example 1-5

| Example | Complexing agent | Molar ratio of complexing agent to metal ions | Calcining temperature (° C.) | Calcining time (h) | Calcining space velocity of air ($h^{-1}$) |
|---|---|---|---|---|---|
| 1 | tartaric acid | 2:1 | 520 | 4 | 80 |
| 2 | citric acid | 1:1 | 500 | 2 | 100 |
| 3 | oxalic acid | 1.5:1 | 490 | 7 | 50 |
| 4 | iminodiacetic acid | 2.5:1 | 530 | 3 | 60 |
| 5 | ethylenediamine tetraacetic acid | 0.5:1 | 510 | 5 | 200 |

Fill 50 g calcined catalyst into a fixed-bed tube reactor, and pump in preheated raw gas comprising isobutene, air nitrogen and steam. The molar ratio of the isobutene, oxygen, water, nitrogen is 1:2:1:1.4. The space velocity of the raw gas is 1500 $h^{-1}$. The oxidation reaction is operated at atmospheric pressure. The reaction conditions and results after 100 hours are listed in Table 2.

TABLE 2 reaction conditions and results of example 1-5

| Example | Salt bath temperature (° C.) | Hot spot temperature (° C.) | Conversion of isobutene (%) | Selectivity to methacrolein (%) | Selectivity to methacrylic acid (%) |
|---|---|---|---|---|---|
| 1 | 365 | 397 | 98.9 | 88.5 | 2.3 |
| 2 | 360 | 394 | 98.8 | 89.1 | 2.7 |
| 3 | 370 | 404 | 98.7 | 90.2 | 3.1 |
| 4 | 360 | 393 | 99.0 | 88.1 | 3.6 |
| 5 | 355 | 387 | 98.5 | 91.1 | 2.1 |

EXAMPLE 6-8

Dissolve 1000 g ammonium heptamolybdate and a certain amount of citric acid in 1 liter distilled water to obtain solution A; Dissolve a certain amount of bismuth nitrate pentahydrate, ferric nitrate ninehydrate, cobalt nitrate hexahydrate, and precursor salt of other component in 1 liter distilled water to obtain solution B. Add solution A into solution B, and keep stirring at 70° C. for 4 hours to obtain a slurry. Then transfer the slurry into an oven of 170° C. for 12 hours to obtain a dry pulp. Mix the dry pulp and a certain amount of heat conduction agent powder mechanically, and mold the mixture into hollow column shape granules with 5 mm outer diameter, 2 mm inner diameter and 3 mm length. Calcine the granules in air to obtain a catalyst. While calcining, the space velocity of air is 100 $h^{-1}$.

The composition and calcining conditions of the catalyst are shown in Table 3.

TABLE 3 composition and calcining conditions of catalyst of example 6-8

| Example | Molar ratio of citric acid to metal ions | Composition of catalyst | Calcining temperature (° C.) | Calcining time (h) |
|---|---|---|---|---|
| 6 | 2:1 | $90(Mo_{12}Bi_{1.5}Fe_{3.0}Co_{6.0}Zn_{1.2}K_{0.1})/$ 10C (graphite) | 520 | 5 |
| 7 | 3:1 | $80(Mo_{12}Bi_{1.0}Fe_{2.5}Co_{5.3}Mn_{1.8}K_{0.2})/$ 20C (carbon fiber) | 515 | 5 |
| 8 | 1:1 | $90(Mo_{12}Bi_{2.5}Fe_{3.5}Co_{5.0}K_{0.3})/$ 10C (carbon fiber) | 520 | 5 |

Fill 50 g calcined catalyst into a fixed-bed tube reactor, and pump in preheated raw gas comprising propylene, air and steam. The molar ratio of propylene, oxygen, water is 1:1.8:1.7. The space velocity of the raw gas is 1000 $h^{-1}$. The oxidation reaction is operated at atmospheric pressure. The reaction conditions and results after 100 hours are listed in Table 4.

TABLE 4 reaction conditions and results of example 6-8

| Example | Salt bath temperature (° C.) | Hot spot temperature (° C.) | Conversion of propylene (%) | Selectivity to acrolein (%) | Selectivity to acrylic acid (%) |
|---|---|---|---|---|---|
| 6 | 325 | 391 | 98.2 | 80.1 | 11.1 |
| 7 | 320 | 380 | 98.0 | 80.9 | 10.9 |
| 8 | 315 | 387 | 98.4 | 82.3 | 10.5 |

EXAMPLE 9-10

Dissolve 1000 g ammonium heptamolybdate in 3 liter distilled water to obtain solution A; Dissolve a certain amount of bismuth nitrate pentahydrate, ferric nitrate ninehydrate, cobalt nitrate hexahydrate, precursor salt of other component and tartaric acid in 0.5 liter distilled water to obtain solution B. Add solution A into solution B, and keep stirring at 40° C. for 6 hours to obtain a slurry. Then transfer the slurry into an oven of 70° C. for 24 hours to obtain a dry pulp. Mix the dry pulp and a certain amount of heat conduction agent powder mechanically, and mold the mixture into hollow column shape granules with 5 mm outer diameter, 2 mm inner diameter and 3 mm length. Calcine the granules in air for 5 hours to obtain a catalyst. While calcination, the space velocity of air is 500 $h^{-1}$.

The composition and calcining conditions of the catalyst of example 9-10 are shown in Table 5.

TABLE 5 composition and calcining conditions of catalyst of example 9-10

| Example | Composition of catalyst | Calcining temperature (° C.) | Calcining time (h) |
|---|---|---|---|
| 9 | 70($Mo_{12}Bi_{3.5}Fe_{1.5}Co_{4.5}Sn_{0.5}Cs_{0.02}$)/30SiC | 500 | 3 |
| 10 | 75($Mo_{12}Bi_{2.0}Fe_{5.5}Co_{4.0}Rb_{0.02}$)/25Si | 510 | 5 |

Fill 60 g calcined catalyst into a fixed-bed tube reactor, and pump in preheated raw gas comprising isobutene, air, nitrogen and steam. The molar ratio of isobutene, oxygen, water, nitrogen is 1:2:1.5:12. The space velocity of the raw gas is 1300 $h^{-1}$. The oxidation reaction is operated at atmospheric pressure. The reaction conditions and results after 100 hours are listed in Table 6.

TABLE 6 reaction conditions and results of example 9-10

| Example | Salt bath temperature (° C.) | Hot spot temperature (° C.) | Conversion of isobutene (%) | Selectivity to methacrolein (%) | Selectivity to methacrylic acid (%) |
|---|---|---|---|---|---|
| 9 | 360 | 395 | 98.7 | 89.7 | 3.5 |
| 10 | 370 | 392 | 98.5 | 90.2 | 2.4 |

EXAMPLE 11

Fill 60 g catalyst obtained in example 3 into a fixed-bed tube reactor for selective oxidation of isobutene to methacrolein. Investigate the stability of the catalyst over a long period. The reaction is under atmospheric pressure and at 370° C. The molar ratio of the raw gas is isobutene:$O_2$:$H_2O$:$N_2$=1:2:1:14. The space velocity of the raw gas is 1500 $h^{-1}$. The results of different reaction periods are shown in Table 7.

EXAMPLE 12

Fill 60 g catalyst in example 8 into a fixed-bed tube reactor for selective oxidation of propylene to acrolein. Investigate the stability of the catalyst over a long period. The reaction is under atmospheric pressure and at 315° C. The molar ratio of the raw gas is propylene:$O_2$:$H_2O$=1:1.8:1.7. The space velocity of the raw gas is 1000 $h^{-1}$. The results of different reaction periods are shown in Table 7.

TABLE 7 reaction periods and results

| Example | Reaction period (h) | Conversion of propylene (%) | Selectivity to acrolein (%) | Selectivity to acrylic acid (%) |
|---|---|---|---|---|
| 11 | 2000 | 99.3 | 89.7 | 2.7 |
|  | 4000 | 98.9 | 89.3 | 3.1 |
|  | 5000 | 99.1 | 90.1 | 2.8 |
| 12 | 2000 | 98.4 | 82.0 | 10.5 |
|  | 4000 | 98.5 | 82.7 | 10.2 |
|  | 5000 | 98.2 | 82.5 | 10.0 |

Comparison 1

The preparation process of the catalyst is the same with example 1, except that complexing agent is not added during the preparation process of the catalyst. The initial reaction condition is the same with example 1. The results are shown in Table 8.

Comparison 2

The preparation process of the catalyst is the same with example 6, except that complexing agent is not added during the preparation process of the catalyst. The initial reaction condition is the same with example 6. The result is shown in Table 8.

Comparison 3

The preparation process of the catalyst is the same with example 7, except that the amount of citric acid as complexing agent added during the preparation process of the catalyst is changed. The molar ratio of citric acid to metal ion is 0.2:1. The initial reaction condition is the same with example 7. The results are shown in Table 8.

Comparison 4

The preparation process of the catalyst is the same with example 9, except that the amount of tartaric acid as complexing agent added during the preparation process of the catalyst is changed. The molar ratio of tartaric acid to metal ion is 10:1. The initial reaction condition is the same with example 9. The results are shown in Table 8.

TABLE 8 reaction conditions and results of comparison 1-4

| Comparison | Salt bath temperature (° C.) | Hot spot temperature (° C.) | Conversion (%) | Selectivity to unsaturated aldehyde (%) | Selectivity to unsaturated acid (%) |
| --- | --- | --- | --- | --- | --- |
| 1 | 365 | 396 | 99.1 | 83.5 | 3.4 |
| 2 | 320 | 392 | 97.2 | 76.9 | 11.5 |
| 3 | 320 | 390 | 97.8 | 78.3 | 10.8 |
| 4 | 360 | 388 | 91.7 | 87.9 | 2.1 |

What is claimed is:

1. A complex oxide catalyst for gas phase oxidation of light alkenes to unsaturated aldehydes, having a general formula $x(Mo_{12}Bi_aFe_bCo_cA_dD_eO_f)/yZ$, wherein $Mo_{12}Bi_aFe_bCo_cA_dD_eO_f$ is active components of the catalyst; Mo, Bi, Fe, Co and O represent molybdenum, bismuth, iron, cobalt, and oxygen respectively; A represents at least one selected from a group consisting of W, V, Zn, Cr, Mn, Sn, Pb, B, Te, Ce, La, and Re; D represents at least one selected from a group consisting of K, Rb, Cs, Sr, Mg and Ba; Z is a heat conduction agent of the catalyst; Z is one or more selected from a group consisting of silicon powder, SiC, graphite and carbon fiber; a~e represent an atomic ratio of corresponding elements respectively, a=0.05~8, b=0.05~10, c=0.5~15, d=0.01~5, e=0.01~3; f is the number of oxygen atoms which satisfies the atomic valences of the other elements; x and y represent the amount of the catalyst active components and the heat conduction agent Z, respectively, y/(x+y)=0~70% (weight).

2. A preparation process of the complex oxide catalyst, as recited in claim 1, comprising steps of:

(a) obtaining a mixed solution by dissolving precursor compounds and complexing agent, and stirring the mixed solution at a temperature of from 40 to 90° C. for 0.5 to 7 hours to obtain a slurry;

(b) drying the slurry obtained in step (a) at a temperature of from 80 to 180° C. for 2 to 12 hours to obtain a dry pulp;

(c) mixing the dry pulp and heat conduction agent and molding the mixture to granules; and (d) calcining the granules at a temperature of from 480 to 550° C. for 2 to 7 hours to obtain catalyst.

3. The preparation process, as recited in claim 2, wherein the precursor compound for catalyst comprises molybdate compound selected from a group consisting of molybdic acid, molybdate and molybdenum oxide, alkali metal or alkaline earth metal compound selected from a group consisting of corresponding hydroxide and nitrate, and compound selected form a group consisting of nitrate, acetate, chloride and oxide.

4. The preparation process, as recited in claim 3, wherein the complexing agent is at least one selected from a group consisting of citric acid, oxalic acid, tartaric acid, lactic acid, ethylenediaminetetraacetic acid, iminodiacetic acid and Ethylene glycol diethyl ether diamine tetraacetic acid, wherein the molar ratio of the complexing agent and metal ions of the catalyst is 0.5:1 to 3:1.

5. The preparation process, as recited in claim 4, wherein the granules are calcined in molecular oxygen-containing gas or molecular oxygen-containing diluted gas, wherein the molecular oxygen comes from pure oxygen, rich oxygen or air, and the diluted gas is one or more selected from a group consisting of $N_2$, $H_2O$, He and Ar; volume space velocity of gas relative to the catalyst is from 50 to 1500 $h^{-1}$.

6. The preparation process, as recited in claim 5, wherein the catalyst is used for gas phase oxidation of propylene to acrolein or selective oxidation of isobutene or tert-butyl alcohol to methacrolein, wherein the reaction temperature for methacrolein is below 380° C., and the reaction temperature for acrolein is below 350° C., wherein the reaction temperature is salt bath temperature.

7. The preparation process, as recited in claim 6, wherein when the catalyst is used for gas phase oxidation process of isobutene or tert-butyl alcohol to methacrolein, the gas phase oxidation process comprises steps of: preheating mixed gas of isobutene or tert-butyl alcohol, air or molecular oxygen-containing diluted gas, and steam; subsequently, pumping the preheated gas into a fixed-bed tube reactor to enable selective oxidation, wherein the reaction temperature is ranging from 300 to 380° C., and reaction pressure is 0.1 to 0.5 MPa; an space velocity of the mixed gas is 1000 to 5000 $h^{-1}$; a molar concentration of isobutene or tert-butyl alcohol is 1 to 20%; a molar ratio of steam to isobutene or tert-butyl alcohol is 1 to 15.

8. The preparation process, as recited in claim 6, wherein when the catalyst is used for gas phase oxidation process of propylene to acrolein, the gas phase oxidation process comprises steps of: preheating mixed gas of propylene, air or molecular oxygen-containing diluted gas, and steam; subsequently, pumping the preheated gas into a fixed-bed tube reactor to enable selective oxidation, wherein the reaction temperature is ranging from 280 to 350° C., and reaction pressure is 0.1 to 0.5 MPa; an space velocity of the mixed gas is 800 to 5000 $h^{-1}$; a molar ratio of $O_2$ to propylene is 1 to 10, and a molar ratio of steam to propylene is 1 to 15.

9. The preparation process, as recited in claim 2, wherein the complexing agent is at least one selected from a group consisting of citric acid, oxalic acid, tartaric acid, lactic acid, ethylenediaminetetraacetic acid, iminodiacetic acid and Ethylene glycol diethyl ether diamine tetraacetic acid, wherein the molar ratio of the complexing agent and metal ions of the catalyst is 0.5:1 to 3:1.

10. The preparation process, as recited in claim 2, wherein the granules are calcined in molecular oxygen-containing gas or molecular oxygen-containing diluted gas, wherein the molecular oxygen comes from pure oxygen, rich oxygen or air, and the diluted gas is one or more selected from a group consisting of $N_2$, $H_2O$, He and Ar; volume space velocity of gas relative to the catalyst is from 50 to 1500 $h^{-1}$.

11. The preparation process, as recited in claim 2, wherein the catalyst is used for gas phase oxidation of propylene to acrolein or selective oxidation of isobutene or tert-butyl alcohol to methacrolein, wherein the reaction temperature for methacrolein is below 380° C., and the reaction temperature for acrolein is below 350° C., wherein the reaction temperature is salt bath temperature.

12. The preparation process, as recited in claim 11, wherein when the catalyst is used for gas phase oxidation process of isobutene or tert-butyl alcohol to methacrolein, the gas phase oxidation process comprises steps of: preheating mixed gas of isobutene or tert-butyl alcohol, air or molecular oxygen-containing diluted gas, and steam; subsequently, pumping the preheated gas into a fixed-bed tube reactor to enable selective oxidation, wherein the reaction temperature is ranging from 300 to 380° C., and reaction pressure is 0.1 to 0.5 MPa; an space velocity of the mixed gas is 1000 to 5000 $h^{-1}$; a molar concentration of isobutene or tert-butyl alcohol is 1 to 20%; a molar ratio of steam to isobutene or tert-butyl alcohol is 1 to 15.

13. The preparation process, as recited in claim 11, wherein when the catalyst is used for gas phase oxidation process of propylene to acrolein, the gas phase oxidation process comprises steps of: preheating mixed gas of propylene, air or molecular oxygen-containing diluted gas, and steam; subsequently, pumping the preheated gas into a fixed-bed tube reactor to enable selective oxidation, wherein the reaction temperature is ranging from 280 to 350° C., and reaction pressure is 0.1 to 0.5 MPa; an space velocity of the mixed gas is 800 to 5000 $h^{-1}$; a molar ratio of $O_2$ to propylene is 1 to 10, and a molar ratio of steam to propylene is 1 to 15.

14. A complex oxide catalyst for gas phase oxidation of light alkenes to unsaturated aldehydes, having a general formula $x(Mo_{12}Bi_aFe_bCo_cA_dD_eO_f)/yZ$, wherein $Mo_{12}Bi_aFe_bCo_cA_dD_eO_f$ is active components of the catalyst; Mo, Bi, Fe, Co and O represent molybdenum, bismuth, iron, cobalt, and oxygen respectively; A represents at least one selected from a group consisting of Ni, Zn, Sn, and Mn; D represents at least one selected from a group consisting of K, Rb, and Cs; Z is a heat conduction agent of the catalyst; Z is one or more selected from a group consisting of silicon powder, SiC, graphite and carbon fiber; a~e represent an atomic ratio of corresponding elements respectively, a=0.05~8, b=0.05~10, c=0.5~15, d=0~5, e=0.01~3; f is the number of oxygen atoms which satisfies the atomic valences of the other elements; x and y represent the amount of the catalyst active components and the heat conduction agent Z, respectively, y/(x+y)=0~70% (weight).

15. The complex oxide catalyst, as recited in claim 14, wherein A is Ni, and D is K and Cs.

16. The complex oxide catalyst, as recited in claim 14, wherein A is Zn, and D is K.

17. The complex oxide catalyst, as recited in claim 14, wherein A is Mn, and D is K.

18. The complex oxide catalyst, as recited in claim 14, wherein d=0, and D is K.

19. The complex oxide catalyst, as recited in claim 14, wherein A is Sn, and D is Cs.

20. The complex oxide catalyst, as recited in claim 14, wherein d=0, and D is Rb.

* * * * *